Figure 1:
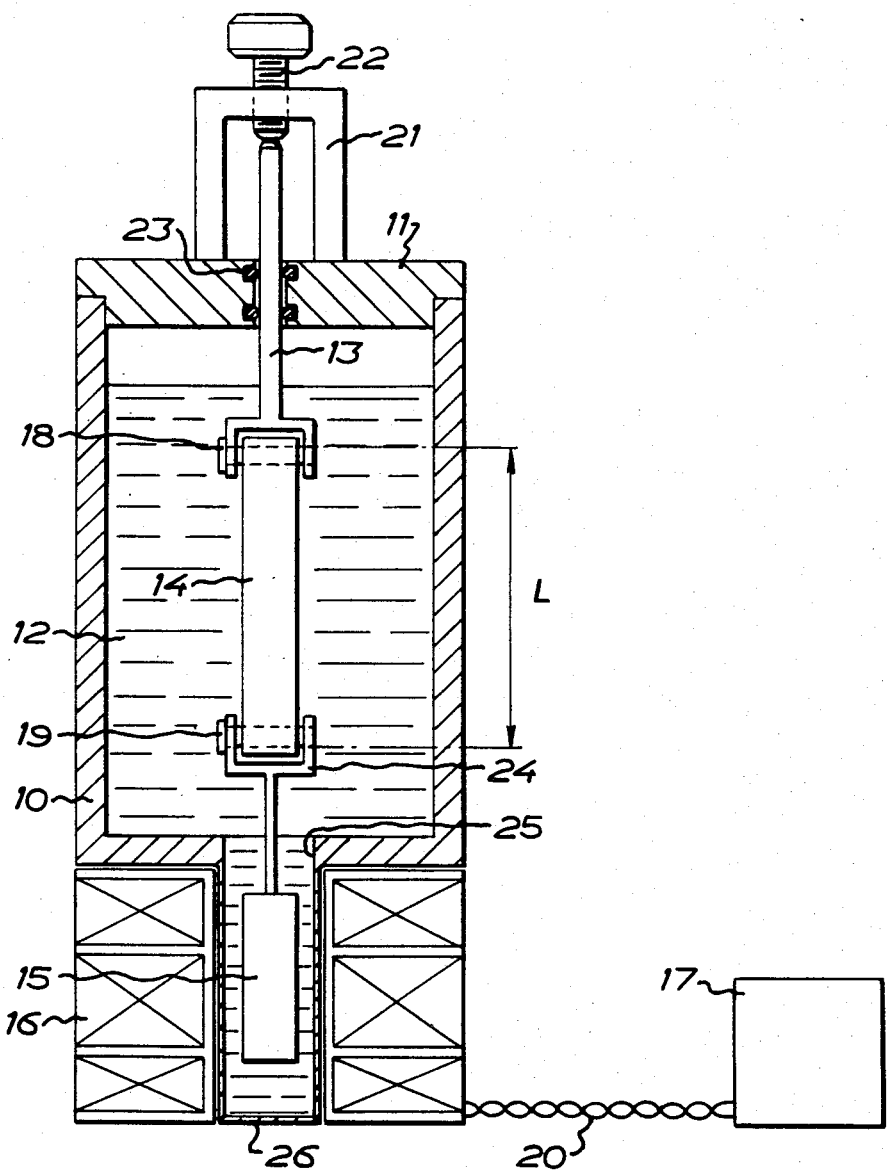

United States Patent [19]

Bohlin

[11] Patent Number: 4,513,611

[45] Date of Patent: Apr. 30, 1985

[54] APPARATUS FOR MEASURING THE SWELLING OR SHRINKAGE OF A SPECIMEN IN A FLUID

[76] Inventor: Leif R. Bohlin, Krankesjövägen 12, S-240 15 Södra Sandby, Sweden

[21] Appl. No.: 527,212

[22] Filed: Aug. 29, 1983

[30] Foreign Application Priority Data

Sep. 1, 1982 [SE] Sweden ................................ 8204977

[51] Int. Cl.³ .............................................. G01N 33/44
[52] U.S. Cl. ................................ 73/150 R; 73/432 PS
[58] Field of Search .............. 73/150, 432 R, 432 SD, 73/432 G, 432 Z, 756

[56] References Cited

FOREIGN PATENT DOCUMENTS 1586740 3/1981 United Kingdom ........... 73/432 SD
853493 8/1981 U.S.S.R. ............................ 73/150 R Primary Examiner—S. Clement Swisher
Attorney, Agent, or Firm—Winburn & Gray, Ltd.

[57] ABSTRACT

An apparatus for measuring the swelling or shrinkage of a specimen in a fluid consists of a container in which the fluid can be accommodated and which has a lid with a suspension device for the specimen, and a transducer which is affixed to the specimen at a location spaced from the point of suspension, for affecting a sensor connected to a recording equipment. In measuring, the movement of the transducer caused by the swelling or shrinkage of the specimen in the fluid can be continuously recorded.

4 Claims, 2 Drawing Figures

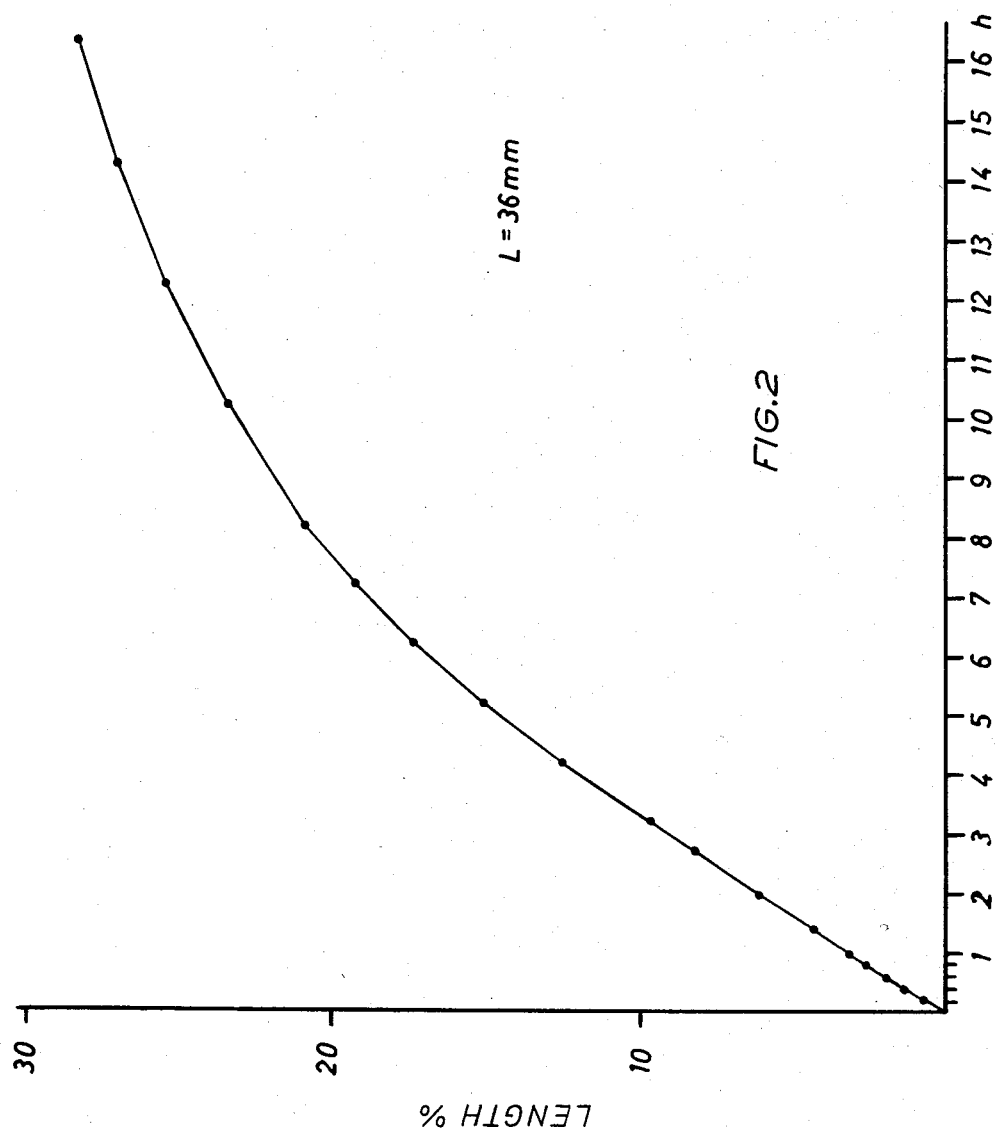

APPARATUS FOR MEASURING THE SWELLING OR SHRINKAGE OF A SPECIMEN IN A FLUID

The present invention relates to an apparatus for measuring the swelling or shrinkage of a specimen in a fluid, comprising a container for accommodating the specimen and the fluid, and a measuring device.

In different technical contexts, it is extremely important to be able to establish to what extent a material swells or shrinks when coming into contact with different fluids. One example is the behaviour of rubber materials in oil or petrol. Attempts have hitherto been made to determine the swelling or shrinkage by placing a specimen of the material to be tested in the fluid and at predetermined time intervals, withdrawing the specimen, wiping it dry and thereafter determining the density by measuring and weighing. It goes without saying that this is a very unreliable method, the result of which depends to a great extent on how the fluid is removed from the specimen before it is weighed and measured, who carries out the weighing and measuring, the time required for weighing and measuring etc.

An apparatus has been developed in order to solve the above-mentioned problems, which comprises a space for holding the fluid and the specimen, and an optical device by means of which the contour of the specimen is projected on a measuring disk. This measuring method, too, is unreliable and it does not permit in a simple fashion to continuously record the changes of the length of the specimen. Besides, this prior art apparatus is expensive.

The object of the present invention is to provide an extremely simple apparatus which makes it possible, with optimum accuracy, to continuously record the changes in length of a specimen placed in a fluid without removing the specimen therefrom.

According to the invention, this object is achieved in that the apparatus comprises means for suspending the specimen in the fluid in the container, a transducer to be affixed to the specimen at a distance from the point of suspension thereof, and a sensor connected to an indicating or recording equipment and adapted to sense the movement of the transducer under the influence of the fluid on the specimen.

The invention will be described in greater detail hereinbelow with reference to the accompanying drawings, in which:

FIG. 1 schematically shows an apparatus according to the invention, and

FIG. 2 is a graph illustrating the swelling of natural rubber in oil-mixed petrol.

The apparatus shown in FIG. 1 for measuring the swelling or shrinkage of a specimen in a fluid comprises a container 10 of a suitable non-magnetizable material, such as metal, plastic or glass. The container 10 has a lid 11 which is connectible to the container 10 by screwing or simply squeezing in place. The container is designed for holding a fluid, e.g. a liquid 12 or a gas, in which latter case it is of course necessary to ensure that the lid 11 can be connected to the container 10 in a gas-tight manner and that appropriate inlet and outlet conduits are provided. At the inner side of the lid 11, there is mounted a fork-shaped suspension member 13 whose shank extends with suitable friction through an opening provided with seals 23 in the lid 11. The upper end of the shank is located underneath a U-shaped member 21 on the upper face of the lid and in a threaded opening in the web of the U-shaped member, there is mounted a screw 22 whose free end engages the end surface of the shaft. By screwing down the screw 22, the shank and thus the entire member 13 will be moved downwards for reasons explained more fully below. A screw 18 extends through one leg of the fork-shaped member 13 and can be screwed into a threaded bore in the other leg of the member 13. A specimen 14 is suspended in the container 10 from the member 13, as will be explained in the greater detail below. A U-shaped holder 24 is connected to the specimen 14 with the aid of a screw 19 which extends through an opening in one leg of the U-shaped holder and an opening in the specimen 14, and can be screwed in a threaded opening in the other leg of the U-shaped holder 24. A transducer 15 of magnetizable metal is connected to the web of the holder 24 and extends down through a central opening 25 in the bottom of the container 10. A cylindrical container extension 26 which is open at the top and made of a non-magnetizable material is tightly connected to the lower end of the opening 25. A differential coil or transformer 16 whose outer diameter substantially corresponds to that of the container 10 is mounted around the container extension 26 which has a considerably smaller diameter than the container 10 and communicates with the interior of the container 10 by the opening 25. The coil 16 is connected by a line 20 to an indicating or recording equipment 17.

When a material is to be tested with respect to swelling or shrinkage in a certain fluid, a specimen 14 is cut from the material and provided with two through-holes at a predetermined distance from each other. The fluid is then poured into the container 10 so as to fill the vessel 26 and reach a predetermined level in the container. With the lid 11 removed, the suspension member 13 and the holder 24 with the transducer 15 are thereafter attached to the specimen 14 in that the screws 18, 19 are passed through the respective holes in the specimen 14 and are tightened. The lid 11 is then applied to the container 10, whereby the specimen 14 suspended from the member 13 is immersed in the fluid in the container 10. The length of the specimen 14 and the distance between its throughholes are so selected that the transducer 15 when immersed will occupy roughly the right location with respect to the differential coil 16. By turning the screw 22 engaging the shaft end of the member 13, the position of the transducer 15 within the coil is then adjusted, while the output signal of the coil is studied. If the fluid in the container 10 affects the specimen 14, for example so as to swell, the length of the specimen 14 will increase, this making the transducer 15 move downwards in the differential coil 16. This movement of the transducer 15 entails that the coil 16 by magnetic induction produces a signal which by the line 20 is applied to the indicating or recording equipment 17. As will appear from the following, the apparatus now described can easily draw a graph showing the change of the length of the specimen during a predetermined period of time. The signal from the coil 16 may also be applied to a computer for the desired processing.

The apparatus now described may of course be modified in many different ways. As earlier pointed out, it can be used for measuring in both liquids and gases. The suspension member 13 is fork-shaped in FIG. 1 but may be designed in many other ways, for instance as a hook from which the specimen 14 is suspended by means of the hole made therein. The holder 24 is U-shaped but may also consist of a hook which is suspended from the other throughhole in the specimen 14. The transducer 15 preferably consists of a magnetizable piece of metal and it is important that it is does not unduly load the specimen 14, for which reason it is made as light as possible or is provided with buoyancy-increasing means, for instance a float or a suitable cavity.

It may sometimes be desirable to heat the liquid in the container 10, in which case the lid 11 is locked to the container with the aid of suitable conventional locking means. In this case, the suspension member 13 is suitably fixed to the inner side of the lid and the adjustment of the position of the transducer 15 may be ensured by suspension members of different length or one such member with adjustable length.

The apparatus according to the invention was used on one occasion to measure the swelling of natural rubber in oil-mixed petrol (4%). For this test, a specimen of natural rubber was first cut out and provided with parallel holes which such a spacing that the distance L (FIG. 1) between the remotest peripheral points of the holes was 36 mm. Oil-mixed petrol was poured into the container 10 to a predetermined level. The transducer 15 and the suspension member 13 were then attached to the specimen 14 in the manner described above, and the lid 11 was applied to the container, so that the specimen 14 with the transducer 15 assumed the position shown in FIG. 1 after adjustment by means of the screw 22. The oil-mixed petrol immediately started affecting the specimen, whereby the transducer 15 was displaced in the coil 16, so that the change in length of the specimen 14 caused by swelling could be recorded by the equipment 17. The swelling was allowed to continue for 16 h and the equipment 17 produced the graph shown in FIG. 2, from which it appears that the influence of the swelling on the longitudinal dimension is very substantial. After a linear initial period, the swelling rate decreased slightly and after 16 h a relative length increase of 28.5% was recorded.

The measurements are carried out, as explained above, with the aid of a transducer of magnetizable metal which affects a differential coil, but it is also conceivable to use other means for this purpose, for instance optical ones.

It will be appreciated from the above that the invention offers an extremely simple and inexpensive apparatus for measuring the swelling or shrinkage of a specimen by continuously measuring the change of length of the specimen. Also, measuring can now be performed with significantly greater reliability than before.

What I claim and desire to secure by Letters Patent is:

1. An apparatus for measuring the effects of fluids such as gases and liquids on swelling or shrinkage of a specimen comprising a container for accommodating the specimen and the fluid; means for suspending the specimen in the fluid in the container; a transducer affixed to the specimen at a distance from the point of suspension thereof such that said transducer is maintained within said fluid and exerts minimized tension on the specimen; and a sensor isolated from the fluid, the sensor being connectable to indicating or recording apparatus and adapted to electromagnetically sense the movement of the transducer under the influence of the fluid on the specimen.

2. Apparatus as claimed in claim 1, further comprising a lid sealing the container, the suspension member includes a hook secured in the lid and insertable in a hole provided in the specimen, the transducer is connected to a suspension hook which is also insertable in and suspendable from a hole provided in the specimen.

3. Apparatus as claimed in claim 1, wherein the suspension member has a shaft extending through the lid and adjustable by longitudinal displacement.

4. Apparatus as claimed in claim 1, wherein the transducer is provided with means for increasing its buoyancy.

* * * * *